United States Patent
Pittman et al.

(10) Patent No.: US 8,563,243 B2
(45) Date of Patent: Oct. 22, 2013

(54) METHODS FOR AFFECTING HOMOLOGY-DIRECTED DNA DOUBLE STRANDED BREAK REPAIR

(75) Inventors: Douglas L. Pittman, Irmo, SC (US);
Brian D. Yard, Toledo, OH (US)

(73) Assignee: University of South Carolina, Columbia, SC (US)

( * ) Notice: Subject to any disclaimer, the term of this patent is extended or adjusted under 35 U.S.C. 154(b) by 163 days.

(21) Appl. No.: 13/105,258

(22) Filed: May 11, 2011

(65) Prior Publication Data

US 2012/0077757 A1    Mar. 29, 2012

Related U.S. Application Data

(60) Provisional application No. 61/333,848, filed on May 12, 2010.

(51) Int. Cl.
*C12Q 1/68* (2006.01)
*C07H 21/02* (2006.01)
*C07H 21/04* (2006.01)
*A61K 31/70* (2006.01)
*C12N 5/00* (2006.01)

(52) U.S. Cl.
USPC ......... 435/6.1; 536/24.1; 536/23.1; 536/24.5; 514/44 A

(58) Field of Classification Search
None
See application file for complete search history.

(56) References Cited

PUBLICATIONS

Zhou et al., Analytical Cellular Pathology vol. 35:167-178, 2012.*
Matsuoka, S et al. *Science*, 316: 1138, 2007.
Yamada, et al., *J. Biol. Chem.*, 281:30, 20749, 2006.
Abstract—Yard et al., "RNF 138, A Novel ubiquitin E3 Ligase is Overexpressed in Colon Cancer Cell Lines and interacts with RAD51 D" *Oasis, The Online Abstract Submission System*, Dec. 1, 20009.

* cited by examiner

*Primary Examiner* — Sean McGarry
(74) *Attorney, Agent, or Firm* — Dority & Manning, PA

(57) ABSTRACT

Disclosed herein are methods and composition for alteration of the presence, activity, or concentration of RNF138. Disclosed methods can be utilized to affect DNA double strand break repair. Methods and compositions can be utilized to alter RNF138 so as to prevent interaction between RNF138 and RAD51D. Specifically, methods can prevent RNF138-directed ubiquitylation of RAD51D, which is necessary for DNA double strand break repair.

10 Claims, 9 Drawing Sheets

METHODS FOR AFFECTING HOMOLOGY-DIRECTED DNA DOUBLE STRANDED BREAK REPAIR

CROSS REFERENCE TO RELATED APPLICATION

The present application claims filing benefit of U.S. Provisional Application Ser. No. 61/333,848 having a filing date of May 12, 2010, which incorporated herein in by reference its entirety.

SEQUENCE LISTING

The instant application contains a Sequence Listing which has been submitted in ASCII format via EFS-Web and is hereby incorporated by reference in its entirety. Said ASCII copy, created on Jul. 29, 2011, is named USC229.txt and is 2,401 bytes in size.

BACKGROUND OF THE INVENTION

Deficiencies in DNA damage response and repair pathways that manage DNA double-strand breaks (DSBs) are associated with cancer susceptibility. For instance, mutations in either BRCA1 or BRCA2, which are involved in DSB repair through interaction with RAD51 proteins, can lead to a greatly increased risk of developing breast, ovarian, and prostate cancers.

The RAD51 protein family provides core components of the Homologous Recombination (HR) complex, which is critical for repairing DNA double-strand breaks and maintaining genome stability. RAD51D, a member of the RAD51 protein family, is required for homology-directed repair of both DNA DSBs and interstrand crosslinks and maintains chromosome and telomere integrity. RAD51D participates in the "BRCA2 complex" and interacts directly with RAD51C and XRCC2.

Better understanding of the regulation of HR proteins by ubiquitylation processes can provide important insights into cancer progression and guide the identification of new therapeutic strategies. For instance, the development of compounds that regulate HR processes, for example through post-translational modification of the RAD51 paralogs would be of benefit in the art. Identified mediators are potential cancer susceptibility markers or possible chemotherapeutic targets.

SUMMARY

According to one embodiment, disclosed is a method for affecting repair of a DNA double stranded break and/or chromosome stability. For instance, a method can include interacting RNF138 with a second compound, for example siRNA directed at the RNF138. Upon interaction between RNF138 and the second compound, the interaction of RNF138 with RAD51D is modified. A method can also include contacting the RNF138 and RAD51D with DNA that exhibits a double strand break or with a chromosome.

According to one preferred embodiment, a method can be utilized to prevent repair of a DNA double stranded break, for example by prevention of RNF138-directed ubiquitylation of RAD51D.

A method can also include administering a DNA damage reagent to the cell, for instance a cancer cell.

Also disclosed are compositions for affecting repair of DNA double strand breaks. A composition can include a modified RNF138, the RNF138 being modified from natural RNF138 such that interaction between the modified RNF138 and RAD51D differs from the interaction between natural RNF138 and RAD51D. In another embodiment, a composition can include a compound that modifies RNF138, for example siRNA directed to the RNF138.

A composition can include additional components, such as a DNA damage reagent, e.g., a cancer chemotherapy reagent.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures in which:

FIG. 7 discloses SEQ ID NOS 5-8, respectively, in order of appearance.

FIG. 12B—no treatment with MMC in cells that are proficient in RNF128; FIG. 12C—treatment with MMC in cells that are deficient in RNF138; and FIG. 12D—treatment with MMC in cells that are proficient in RNF138.

FIG. 16A is Western analysis and FIG. 16B presents quantification results.

FIG. 17A is Western analysis and FIG. 17B presents quantification results.

DETAILED DESCRIPTION OF REPRESENTATIVE EMBODIMENTS

Reference will now be made in detail to embodiments of the disclosed subject matter, one or more examples of which are set forth below. Each example is provided by way of explanation of the subject matter, not limitation of the subject matter. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

Definitions

For purposes of the present disclosure, the term "polypeptide" generally refers to a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations and the like. The term polypeptides as utilized herein encompasses polypeptides formed according to any known method. For instance, polypeptides can be naturally produced polypeptides, purified polypeptides, recombinant polypeptides, or synthetic polypeptides, as are known in the art.

For purposes of the present disclosure, the term "protein" generally refers to any molecular chain of amino acids that is capable of interacting structurally, enzymatically or otherwise with other proteins, polypeptides or any other organic or inorganic molecule.

For purposes of the present disclosure, the term "ortholog" generally refers to a nucleotide or polypeptide sequence with similar function to a nucleotide or polypeptide sequence in an evolutionarily related species. Loci in two species are said to be "orthologous" when they have arisen from the same locus of their common ancestor. Orthologous polynucleotide sequences exist at loci in different species that are sufficiently similar to each other in their nucleotide sequences to suggest that they originated from a common ancestral sequence. Orthologous sequences arise when a lineage splits into two species, rather than when a sequence is duplicated within a genome. Proteins that are orthologs of each other are encoded by genes of two different species, and the genes are said to be orthologous.

DETAILED DESCRIPTION

In general, the present disclosure is directed to mediators of homology-directed DNA DSB repair and methods for affecting DNA damage repair through knockdown or enhancement of disclosed mediators.

Figure 1:
FIG. 1 is a schematic diagram of the RNF138 protein.

RNF138, schematically illustrated in FIG. 1, includes an N-terminal RING finger E3 ubiquitin ligase domain (RING), three zinc finger domains (ZF), and a putative C-terminal ubiquitin interaction motif (UIM). Presence of both the RING and UIM domains indicates that RNF138 can induce the transfer of ubiquitin to target substrates and can also recognize ubiquitin moieties on other proteins. Ubiquitin signaling is essential for DNA double-strand break repair. The ZF domains contain a cys-his-cys motif that binds one zinc cation. RNF138 has been identified as a candidate for phosphorylation by ATM/ATR following DNA damage (Matsuoka, S et al. *Science*, 316: 1138, 2007).

Yamada, et al. (J. Biol. Chem., 281:30, 20749, 2006) identified RNF138 as an E3 ligase involved in ubiquitylation post-translational modification. In general, ubiquitilation involves a sequential multienzyme reaction directed by E1 ubiquitin-activating enzyme, E2 ubiquitin-conjugating enzyme, and E3 ubiquitin ligase. RNF138 has been shown to associate with the carboxyl terminus of NLK and targets TCF/LEF proteins for ubiquitylation. RNF138-ubiquitylated TCF/LEF is subsequently degraded by the proteasome, resulting in the down-regulation of TCF/LEF-dependent transcriptional activity. Several RNF138 structures have been specifically detailed, including *Xenopus* (GenBank Acc. No. DQ011285), a human ortholog (GenBank Acc. No. NO057355, mouse (GenBank Acc. No. NO997506) and rat (GenBank Acc. No. XP228926).

Figure 2:
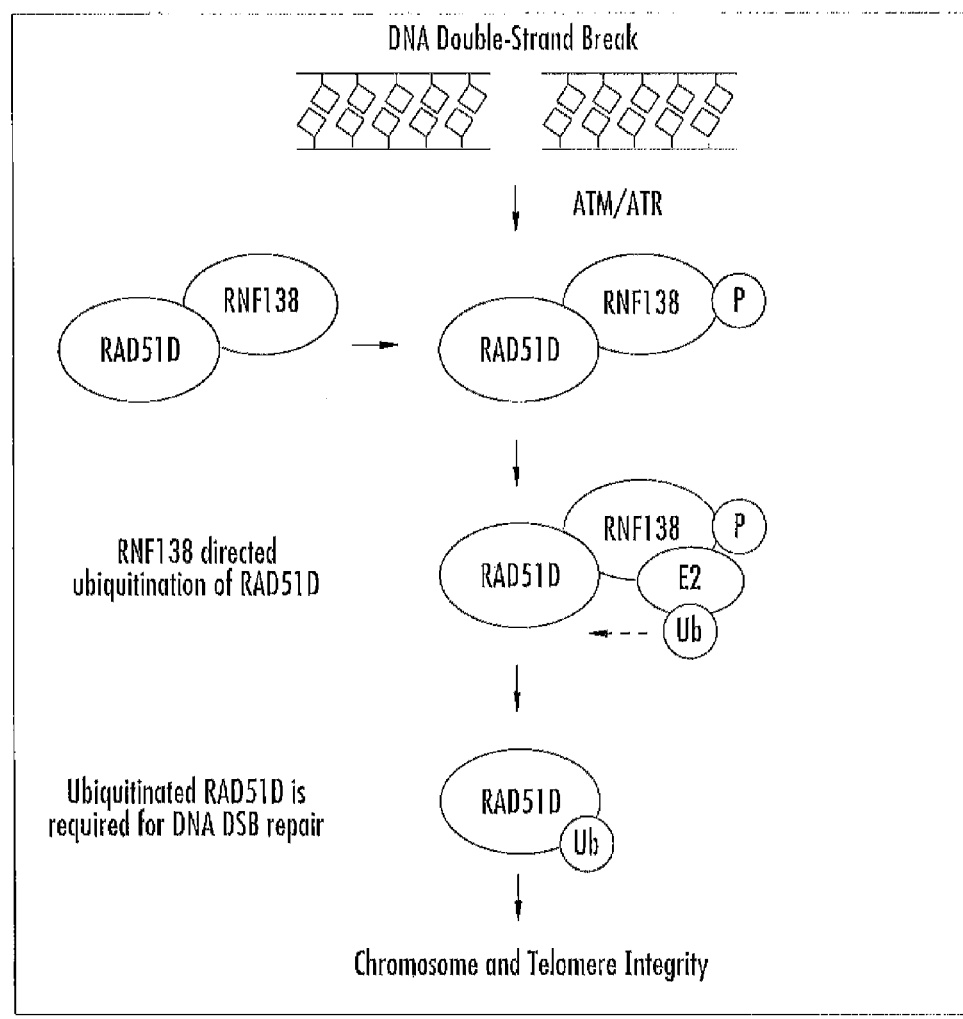
FIG. 2 is a model of RAD51D/RNF138 interaction.

As disclosed herein, RNF138 has been found to interact with RAD51D and is necessary for DNA repair and chromosome stability. Without wishing to be bound by any particular theory, FIG. 2 schematically illustrates a model for this interaction. Specifically, following DNA damage, H2aX is phosphorylated by ATM/ATR in cooperation with MDC1. This also is predicted to lead to the phosphorylation of RNF138 followed by RNF138-directed ubiquitylation of RAD51D, which is required for repair of DNA DSB breaks as well as chromosome and telomere integrity, as is known in the art.

According to the present disclosure, alteration of the presence, activity, or concentration of RNF138 can be utilized to affect DNA repair, for instance DNA double strand breaks (DSB). In one embodiment, disclosed methods can be utilized to affect DNA repair in the presence of a DNA damage reagent, for instance a chemotherapy reagent used in the treatment of cancer. For instance, knockout of RNF138, for instance via siRNA, can impair DNA damage repair in the presence of a DNA damage reagent such as mitomycin C, cisplatin, camptothecin, and the like. Accordingly, disclosed methods can be utilized in various treatment protocols including cancer chemotherapy cancer treatments.

Without wishing to be bound by any particular theory, it is believed that alteration of the presence, activity, or concentration of RNF138 can interfere with the interaction of RNF138 with RAD51D, which, in turn, can interfere with the homology-directed repair of both DNA DSBs and interstrand crosslinks as well as the chromosome stability and telomere integrity that is potentiated by RAD51D.

The present disclosure can be better understood with reference to the Examples, provided below.

Example 1

A yeast two-hybrid screen was performed using the RAD51 paralogs RAD51C, RAD51D, and XRCC2 as bait against a normalized universal mouse cDNA library. Fifty-eight primary candidates were isolated, five of which were predicted to function in the ubiquitylation pathway. Within this group, RNF138 was of particular interest due to the inclusion of both an N-terminal RING fiber domain and a putative C-terminal ubiquitin interaction motif. Accordingly, RNF138, was examined further as described herein.

Figure 3:
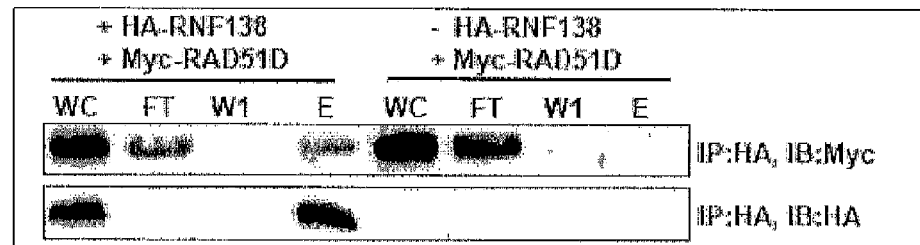
FIG. 3 illustrates results showing interaction of RNF138 and RAD51D in mammalian cells.

Constructs encoding HA-RNF138 and Myc-RAD51D were transiently transfected into HeLa cells. After 24 hours, whole cell extracts were subject to immunoprecipitation using anti-HA sepharose beads and analyzed by immunoblotting with anti-HA and anti-Myc antibodies. Results are illustrated in FIG. 3. As can be seen, RNF138 and RAD51D interact in the mammalian cells.

Example 2

Yeast two-hybrid protocols were carried out. Y187 yeast haploids were utilized, and beta-galactosidase activity was measured using the ONPG assay, as is known.

Figure 4:
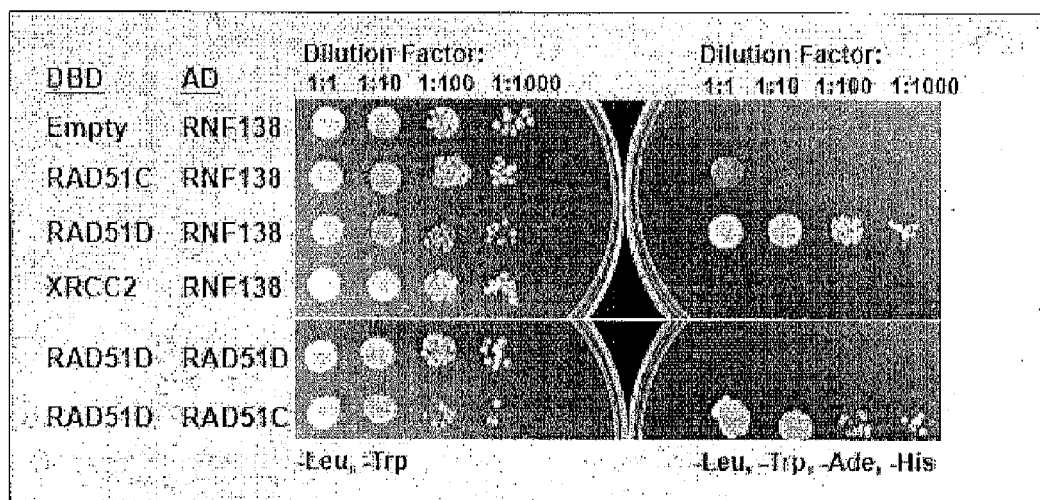
FIG. 4 illustrates the results of yeast two-hybrid assays comparing interaction of RNF138 with RAD51D, RAD51C, and XRCC2.

Interaction between RNF138 and RAD51C, RAD51D, and XRCC2 was examined. Results, illustrated in FIG. 4, indicate that RNF138 interaction is unique to RAD51D, as RNF138 failed to directly interact with RAD51C and XRCC2. Controls included an empty/RNF138 negative control, RAD51D/RAD51D negative control, and RAD51D/RAD51C positive control.

Figure 5:
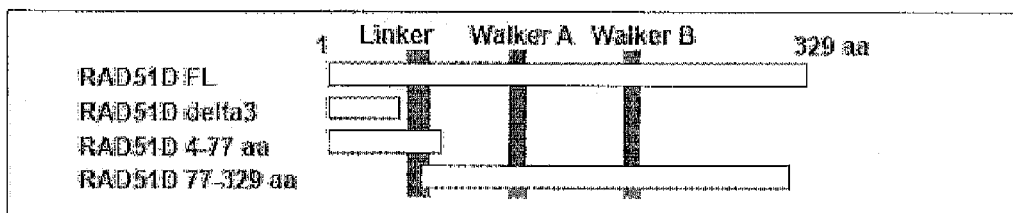
FIG. 5 illustrates truncated RAD51D constructs utilized in a yeast two-hybrid assay.

Further analysis was carried out using N- and C-terminal truncated RAD51D constructs (FIG. 5). Results (FIG. 6) revealed that the RAD51D core domain rather than the N-terminal linker region that governs the interaction between RAD51D and XRCC2 mediates the association with RNF138.

Figure 6:
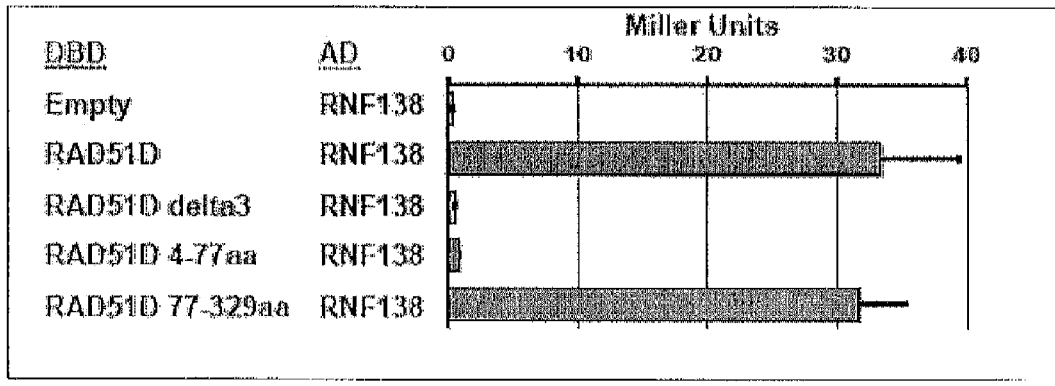
FIG. 6 illustrates the results of a yeast two-hybrid assay comparing interaction of RNF138 with each of the different constructs of FIG. 5.
Figure 7:
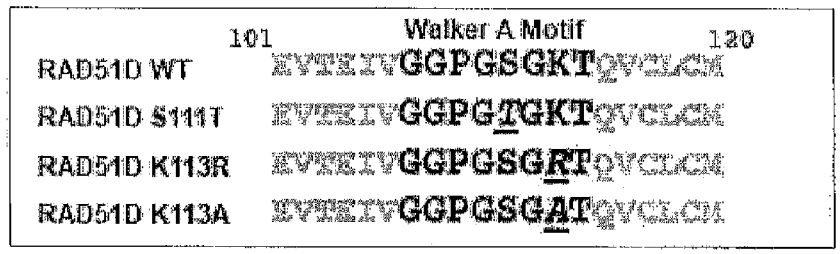
FIG. 7 illustrates mutations of the highly conserved RAD51 D Walker A ATP binding motif utilized in a yeast two-hybrid assay.
Figure 8:
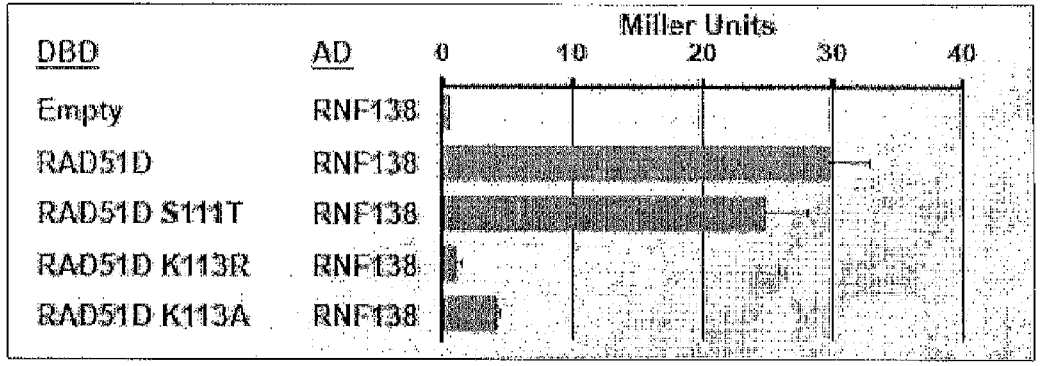
FIG. 8 illustrates the results of a yeast two-hybrid assay comparing interaction of RNF138 with each of the different constructs of FIG. 7.

Additionally, analysis was carried out utilized K113A and K113R mutations of the highly conserved RAD51D Walker A ATP binding motif as shown in FIG. 7. As can be seen in the results (FIG. 8), the mutations abolished RAD51D-RNF138 association, suggesting that ATP binding and hydrolysis may regulate the interaction. (Error bars on FIGS. 6 and 8 represent SEM of 3 independent experiments performed in triplicate.)

Example 3

RNF138 mRNA expression was normalized to both β-Actin and Gapdh mRNA expression. (Error bars represent SD from a representative experiment performed in triplicate.) Two mouse fibroblast cell lines were utilized. One line (Rad51d$^{+/+}$) had a normal Rad51d gene. The other line (Rad51D$^{-/-}$) had a deletion of the Rad51d gene and was therefore deficient for HR. These lines were used as a control.

Figure 9:
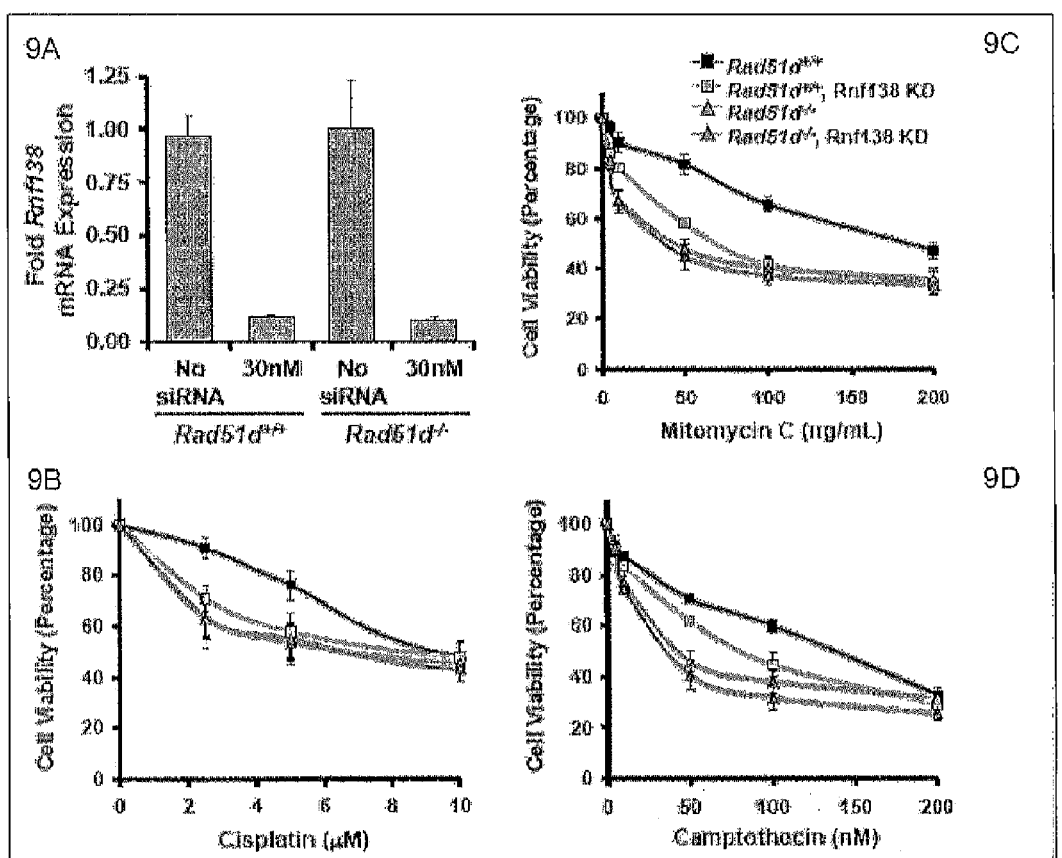
FIG. 9 illustrates the effect of RNF138 knockdown on cell viability following treatment with various DNA damage reagents.

Mouse embryonic fibroblasts (MEFs) were treated with three different DNA damage reagents. DNA damage was assessed 24 hr after transfection with 30 nM Rnf138 siRNA (FIG. 9A). siRNA was purchased from Sigma-Aldrich. Cell viability was measured 7 days following treatment with mitomycin C (FIG. 9B), cisplatin (FIG. 9C), or camptothecin (FIG. 9D) by the MTT assay. Error bars represent SEM of 4 independent experiments performed in quadruplicate. The results indicate that Rad51d and Rnf138 function in the same part of the DNA repair pathway. This further illustrates Rnf138 specialized functions.

Example 4

Figure 10:
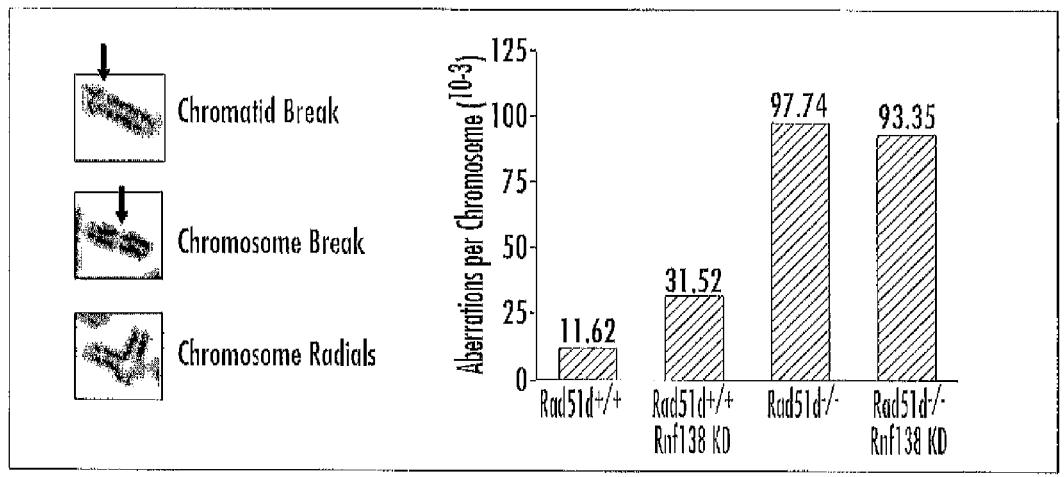
FIG. 10 illustrates the effect of RNF138 knockdown on chromosome stability.

MEFs were treated for 6 hr with Mitomycin C (50 ng/mL) 24 hr after transfection with or without 30 nM Rnf138 siRNA. Total number of aberrations (chromatid breaks and gaps, chromosome breaks, and chromosome radials) were counted from Geimsa stained metaphase spreads 48 hr following treatment. At least 1000 chromosomes were examined per treatment group. Results are illustrated in FIG. 10.

Example 5

Figure 11:
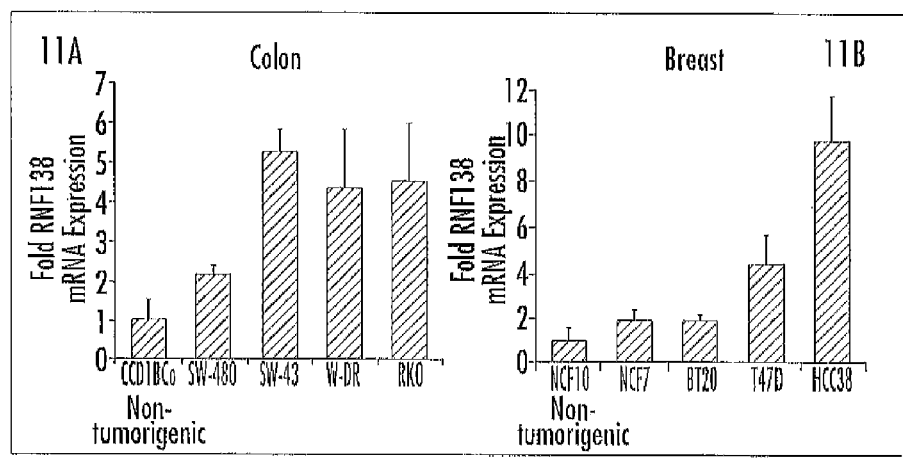
FIG. 11 illustrates RNF138 expression in colon (FIG. 11A) and breast (FIG. 11B) cancer cell lines.

RNF138 mRNA expression was analyzed by quantitative RT-PCR and normalized to GAPDH mRNA expression in SW-48, RKO, and Wi-DR colon cancer cell lines (FIG. 11A) and HCC38 breast cancer cell line (FIG. 11B). Error bars represent standard deviation from two independent experiments performed in triplicate. Expression of RNF138 was found to be increased by 12-fold in the breast cancer cell line and 4-fold in the colon cancer cell lines compared to non-tumorigenic controls.

Example 6

The presence of RAD51 foci was examined in MEFs subjected to either 200 ng/mL Mitomycin C (MMC) treatment or with no treatment. In addition, both deficient RNF138 cells and proficient RNF138 cells were examined.

For analysis of RAD51 foci formation, 10,000 cells were seeded onto glass coverslips for transfection with Rnf 138 siRNA. Twenty-four hr following siRNA transfection, cells were challenged with MMC (200 ng/mL) for 16 hr. Immunofluoresence detection of RAD51 foci was carried out as is generally known I the art (see, e.g., Smiraldo et al., 2005). Cells containing five or more distinct foci were scored positive. For each condition, a minimum of 250 cells from at least three independent experiments was analyzed (n≥750).

Figure 12:
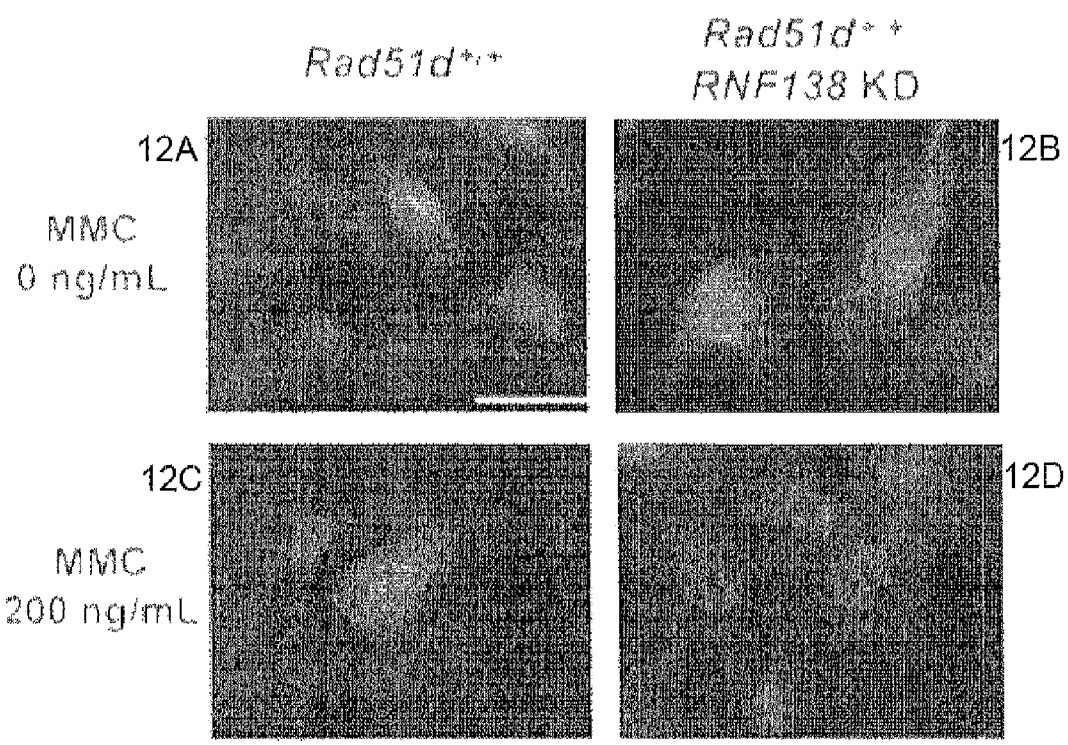
FIGS. 12A-12D illustrate immunofluorescence visualization of RAD51 foci in Rad51 $d^{+/+}$ (Rad51$d^{+/+}$, Trp53$^{-/-}$) in mouse embryonic fibroblasts including FIG. 12A—no treatment with Mitomyocin C (MMC) in cells that are deficient in RNF138.
Figure 13:
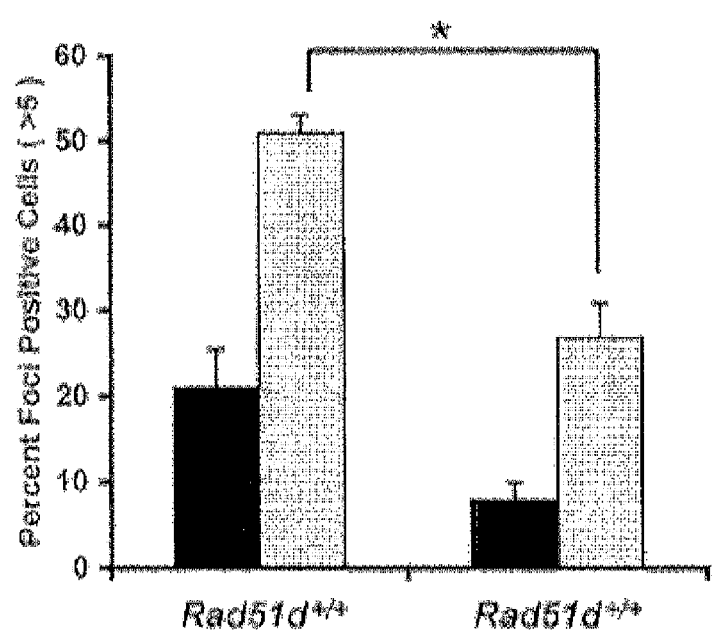
FIG. 13 illustrates quantification of RAD51 foci formation visualized in FIG. 12. Data represent mean+/−SEM from three independent experiments and * indicates P<0.05.

The presence of RAD51 foci monitored by immunofluorescence is illustrated in FIGS. 12A-D. RAD51 foci indicates DNA damaged sites undergoing HR repair. MMC treatment (200 ng/mL) increased the percentage of cells containing 5 or more distinct RAD51 foci from approximately 21 percent for untreated control cells (FIG. 12B) to 51 percent (FIG. 12D) following a 16 h exposure (p<0.01). Reduced RNF138 expression however, resulted in a 1.9-fold decrease in RAD51 foci formation following MMC treatment (p<0.05) (FIG. 12C). In addition, RAD51 foci formation was less in untreated RNF138 deficient (FIG. 12A) versus RNF138 proficient (FIG. 12B) MEFs. Although, a notable increase in RAD51 foci is still detected upon MMC treatment (FIG. 13).

Figure 14:
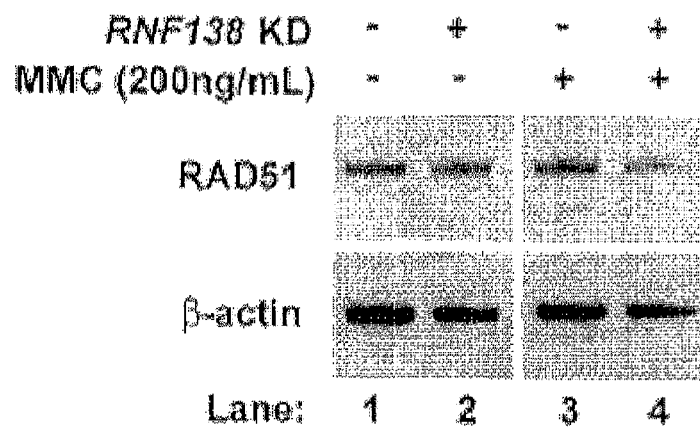
FIG. 14 is Western analysis of RAD51 protein levels in the four samples of FIG. 12. β-actin was used as a loading control and the RAD51 band intensity was normalized to β-actin.

Western analysis (FIG. 14) confirmed that depletion of RNF138 had no significant effect on RAD51 protein levels. Western blot analysis was performed using mouse monoclonal anti-HA (3F10; Roche) and mouse monoclonal anti-Myc (9E10; Santa Cruz Biotechnology). Primary antibody incubation was followed by incubation with the appropriate species-specific HRP-conjugated secondary antibody (Santa Cruz Biotechnology) and detection using ECL (West-Pico chemiluminescent substrate; Thermo-Scientific). Quantitative analysis of band intensity was performed using NIH ImageJ 1.43u software. As can be seen, the data indicate that RNF138 is needed for RAD51 foci formation and HR repair of DNA damage.

Example 7

The determination of direct interaction between RNF138 and RAD51D suggested that RNF138 might target RAD51D for ubiquitination. To examine this, HA-RAD51D, Myc-Ubiquitin, and Myc-RNF138 were expressed in mammalian cells and anti-HA immunoprecipitation performed (FIG. 15).

Specifically, RNF138 (MmRnf138 NM_207623.1) expression vectors were generated by PCR amplification of mouse liver cDNA with Platinum Taq DNA Polymerase High Fidelity (available from Invitrogen) using MmRnf138-specific primers RNF138s1 (5'-CTTGGTACCTCCGAG-GAACTTTCGGCGG-3') (SEQ ID NO: 1) and RNF138as1 (5'-CTTGGATCCTGTAGGTTGCAAGGAGGCAG-3') (SEQ ID NO: 2) followed by cloning of the amplification products into the KpnI/BamHI sites of pcDNA3.1/Hygro+ (available from Invitrogen) with either HA or Myc epitope tags. Mutagenesis of the RNF138 RING finger domain (H36A,C39S) was accomplished by subcloning MmRnf138 cDNA into pUC19 for conventional PCR based site-directed mutagenesis with primers: RNF138mut1 (5'-GGCCTGT-CAGgcCGTTTTCTcTAGAAAATGTTT CCTGACTG-3') (SEQ ID NO: 3) and RNF138mut2 (5' CAGTCAGGAAA-CATTTTCTAgAGAAAA CGgcCTGACAGGCC 3') (SEQ ID NO: 4). The small case portion denotes sequence targeted for mutagenesis. All PCR derived expression constructs were confirmed by sequencing both strands. The Myc-ubiquitin expression vector was provided by Dr. Xiongbin Lu (Department of Cancer Biology, M D Anderson).

For co-immunoprecipitations, vectors encoding HA-tagged and Myc-tagged proteins were co-transfected into HeLa cells. Whole cell extracts were prepared after 24 h using mammalian protein extraction reagent (M-PER; Thermo-Scientific) containing a protease inhibitor cocktail (Complete Mini; Roche Life Sciences). Five hundred micrograms of whole cell extract was incubated with anti-HA agarose beads (3F10; Roche) for 16 h at 4° C. with gentle rocking. Precipitated proteins were washed 3 times with 1×PBST, eluted by boiling in Laemmli buffer for 10 minutes, and resolved on 12% SDS-PAGE. For in-vivo ubiquitination assays, cells were treated with 25 µM MG132 (Sigma) 4 h prior to preparation of whole cell extracts. Incubation of extract with anti-HA agarose beads was carried out for 6 h at 4° C.

Figure 15:
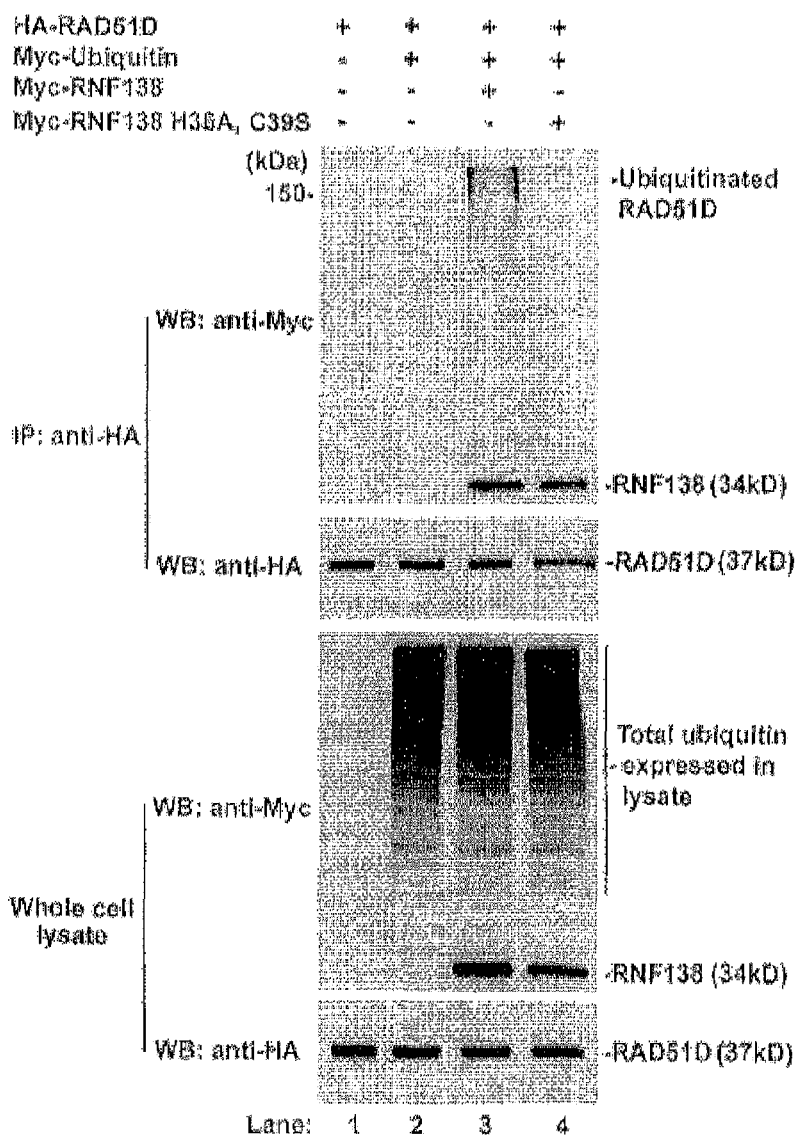
FIG. 15 illustrates immunoprecipitation analysis demonstrating RNF138 facilitation of RAD51D ubiquitination in vivo.

As may be seen in FIG. 15, ubiquitinated. HA-RAD51D was observed following RNF138 overexpression, but not under endogenous RNF138 levels (lane 2 vs 3). Ubiquitinated RAD51D migrated as a high molecular weight smear indicating that RAD51D was polyubiquitinated at one or more sites. However, the RNF138 E3 ligase null mutant (H36A, C39S) was unable to mediate RAD51D ubiquitination (lane 4) despite retaining the ability to interact with RAD51D. Thus, RNF138 E3 ligase activity is responsible for RAD51D ubiquitination.

Figure 16:
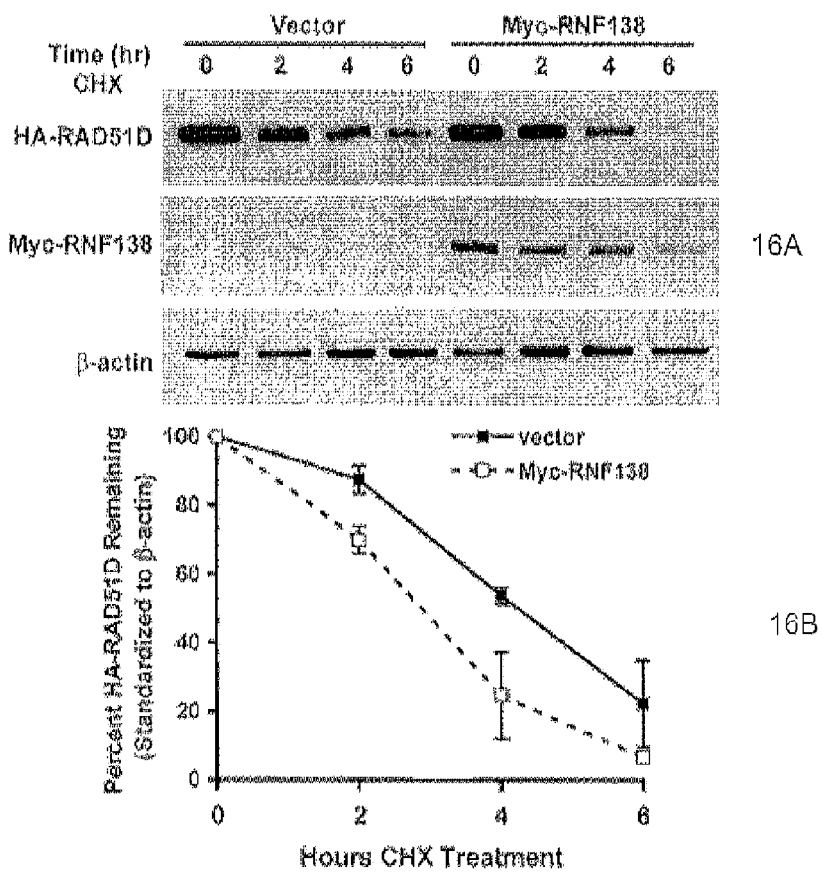
FIG. 16 illustrates analysis of Rad51d$^{-/-}$ Trp53$^{-/-}$ HARad51d MEFs that were transfected with Myc-RNF138. HA-RAD51D protein levels were assessed 2, 4, and 6 hours following initiation of CHX block. HA-RAD51D band intensity was normalized to β-actin and plotted as percent protein remaining for each time point. Data represent mean+/−STD from two representative experiments.
Figure 17:
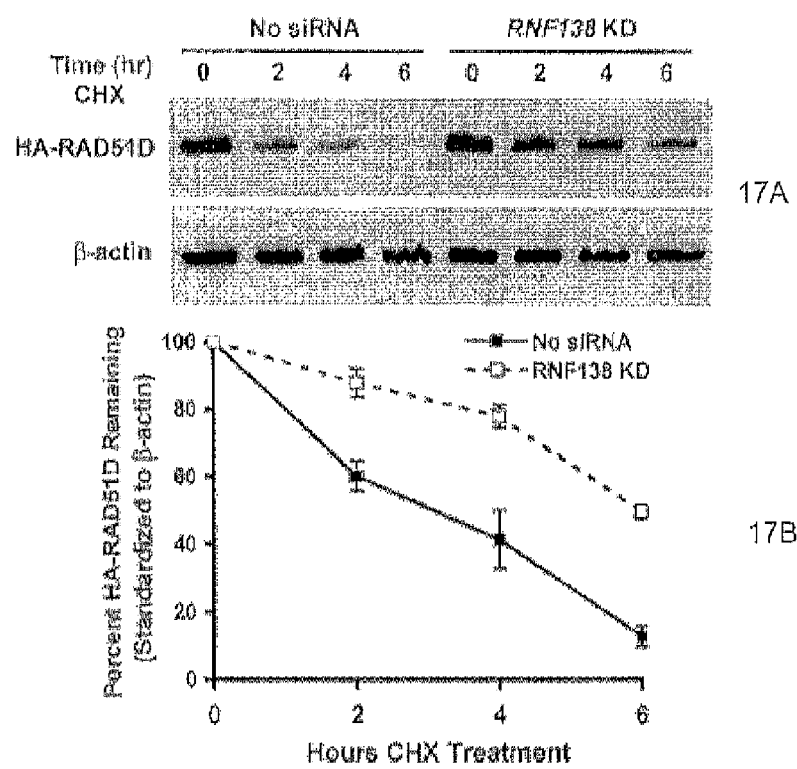
FIG. 17 illustrates analysis of Rad51d$^{-/-}$ Trp53$^{-/-}$ HARad51d MEFs that were transfected with 30 nM Rnf138 siRNA1. HA-RAD51D protein levels were assessed 2, 4, and 6 hours following initiation of CHX block. HA-RAD51D band intensity was normalized to β-actin and plotted as percent protein remaining for each time point. Data represent mean+/-STD from two representative experiments.

To determine whether RNF138-directed ubiquitination modulates RAD51D protein stability, RAD51D half-life was examined in cells stably expressing HA-RAD51D (FIG. 16A). As illustrated, increased RNF138 expression shortened HA-RAD51D half-life from 4.2 hours to 3.0 hours (FIG. 16B). Likewise, depletion of endogenous RNF138 by siRNA resulted in an accumulation of HA-RAD51D protein (FIG. 17A) and extended HA-RAD51D half-life to 6.6 hours (FIG. 17B). These data indicate RNF138-mediated ubiquitination of RAD51D negatively regulates RAD51D protein levels.

Figure 18:
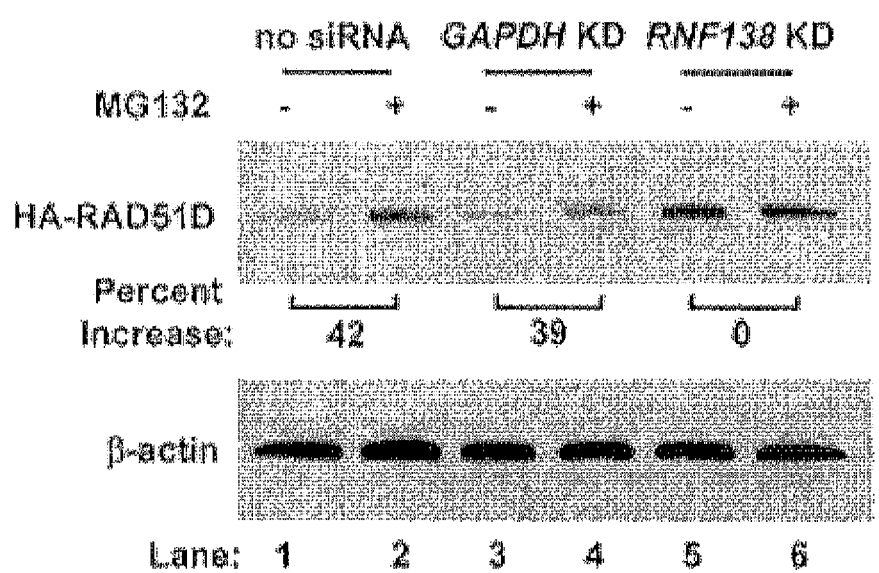
FIG. 18 illustrates analysis of MEFs that were treated with CHX (100 mg/mL) or CHX in combination with MG132 (20 mg/mL). Cell lysates were prepared at the 4 hour time point, and HA-RAD51D band intensity was calculated as described herein.

To determine whether decreased HA-RAD51D half-life can be attributed to proteasome degradation, HA-RAD51D protein levels were assessed following treatment with the proteasome inhibitor MG132. As anticipated, HA-RAD51D protein levels were elevated up to 42% in MG132 treated samples (FIG. 18, lanes 1-4) indicating RAD51D protein levels are in part regulated by the proteasome. Intriguingly, proteasome inhibition failed to increase HA-RAD51D protein stability following knockdown of RNF138 expression (FIG. 18, lanes 5-6). This result implies that in the absence of RNF138, RAD51D ubiquitination is diminished and as a result, RAD51D is not targeted for proteasome degradation.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method for affecting repair of a DNA double stranded break comprising:
    interacting a proficient RNF138 cell with Rnf138 siRNA, the proficient RNF138 cell including DNA with a double stranded break, wherein upon interaction between the proficient RNF138 cell and the Rnf138 siRNA, the expression of RNF138 is reduced, and;
    wherein following interaction between the cell and the Rnf138 siRNA, the repair of the DNA double stranded break is decreased.

2. The method according to claim 1, wherein the interaction between the cell and the Rnf138 siRNA prevents RNF138-directed ubiquitylation of the RAD51D.

3. The method according to claim 1, the method further comprising administering a DNA damage reagent to the cell.

4. The method according to claim 3, wherein the cell is a cancer cell.

5. The method according to claim 4, wherein the cell is a breast cancer cell or a colon cancer cell.

6. A method for affecting chromosome stability comprising:
    interacting a proficient RNF138 cell with Rnf138 siRNA, the cell including a chromosome with a double stranded break wherein upon interaction between the proficient RNF138 cell and the Rnf138 siRNA, the expression of RNF138 is reduced and a repair of the DNA double stranded break on the chromosome of the cell is prevented.

7. The method according to claim 6, wherein the interaction between the proficient RNF138 cell and the Rnf138 siRNA prevents RNF138-directed ubiquitylation of RAD51D.

8. The method according to claim 6 the method further comprising administering a DNA damage reagent to the cell.

9. The method according to claim 8, wherein the cell is a cancer cell.

10. The method according to claim 9, wherein the cell is a breast cancer cell, or a colon cancer cell.

* * * * *

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cttggtacct ccgaggaact ttcggcgg                                          28

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttggatcct gtaggttgca aggaggcag                                         29
```

-continued

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcctgtcag gccgttttct ctagaaaatg tttcctgact g                          41

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtcaggaa acattttcta gagaaaacgg cctgacaggc c                          41

<210> SEQ ID NO 5
<211> LENGTH: 20
<212> TYPE: PRT
<213> ORGANISM: Unknown
<220> FEATURE:
<223> OTHER INFORMATION: Description of Unknown: RAD51D WT peptide

<400> SEQUENCE: 5

Glu Val Thr Glu Ile Val Gly Gly Pro Gly Ser Gly Lys Thr Gln Val
1               5                   10                  15

Cys Leu Cys Met
            20

<210> SEQ ID NO 6
<211> LENGTH: 20
<212> TYPE: PRT
<213> ORGANISM: Unknown
<220> FEATURE:
<223> OTHER INFORMATION: Description of Unknown: RAD51D S111T peptide

<400> SEQUENCE: 6

Glu Val Thr Glu Ile Val Gly Gly Pro Gly Thr Gly Lys Thr Gln Val
1               5                   10                  15

Cys Leu Cys Met
            20

<210> SEQ ID NO 7
<211> LENGTH: 20
<212> TYPE: PRT
<213> ORGANISM: Unknown
<220> FEATURE:
<223> OTHER INFORMATION: Description of Unknown: RAD51D K113R peptide

<400> SEQUENCE: 7

Glu Val Thr Glu Ile Val Gly Gly Pro Gly Ser Gly Arg Thr Gln Val
1               5                   10                  15

Cys Leu Cys Met
            20

<210> SEQ ID NO 8
<211> LENGTH: 20
<212> TYPE: PRT
<213> ORGANISM: Unknown

```
<220> FEATURE:
<223> OTHER INFORMATION: Description of Unknown: RAD51D K113A peptide

<400> SEQUENCE: 8

Glu Val Thr Glu Ile Val Gly Gly Pro Gly Ser Gly Ala Thr Gln Val
1               5                   10                  15

Cys Leu Cys Met
            20
```